US011077076B2

(12) United States Patent
Corr et al.

(10) Patent No.: US 11,077,076 B2
(45) Date of Patent: *Aug. 3, 2021

(54) PHARMACEUTICAL COMPOSITION

(71) Applicant: MEXICHEM FLUOR S.A. DE C.V., San Luis Potosi (MX)

(72) Inventors: Stuart Corr, Warrington (GB); Timothy James Noakes, Flintshire (GB)

(73) Assignee: MEXICHEM FLUOR S.A. DE C.V., San Luis Potosi S.L.P. (MX)

( * ) Notice: Subject to any disclaimer, the term of this patent is extended or adjusted under 35 U.S.C. 154(b) by 0 days.

This patent is subject to a terminal disclaimer.

(21) Appl. No.: 16/883,016

(22) Filed: May 26, 2020

(65) Prior Publication Data

US 2020/0281875 A1 Sep. 10, 2020

Related U.S. Application Data

(62) Division of application No. 16/334,144, filed as application No. PCT/GB2017/052764 on Sep. 18, 2017, now Pat. No. 10,792,256.

(30) Foreign Application Priority Data

Sep. 19, 2016 (GB) ...................................... 1615914
Dec. 2, 2016 (GB) ...................................... 1620517

(51) Int. Cl.
| | | |
|---|---|---|
| *A61K 31/137* | (2006.01) | |
| *A61K 9/00* | (2006.01) | |
| *A61K 9/12* | (2006.01) | |
| *A61K 31/439* | (2006.01) | |
| *A61K 31/573* | (2006.01) | |
| *A61K 47/14* | (2017.01) | |
| *A61K 47/24* | (2006.01) | |
| *A61K 47/32* | (2006.01) | |
| *A61K 31/56* | (2006.01) | |
| *A61K 45/06* | (2006.01) | |
| *A61P 11/00* | (2006.01) | |

(52) U.S. Cl.
CPC ............ *A61K 31/137* (2013.01); *A61K 9/008* (2013.01); *A61K 9/0078* (2013.01); *A61K 9/124* (2013.01); *A61K 31/439* (2013.01); *A61K 31/56* (2013.01); *A61K 31/573* (2013.01); *A61K 45/06* (2013.01); *A61K 47/14* (2013.01); *A61K 47/24* (2013.01); *A61K 47/32* (2013.01); *A61P 11/00* (2018.01)

(58) Field of Classification Search
CPC ....... A61P 11/00; A61K 9/008; A61K 31/573; A61K 47/24; A61K 45/06; A61K 31/56; A61K 31/137; A61K 9/124; A61K 31/439; A61K 47/14; A61K 47/32; A61K 9/0078

See application file for complete search history.

(56) References Cited

U.S. PATENT DOCUMENTS

| | | | |
|---|---|---|---|
| 5,439,670 A | 8/1995 | Purewal et al. | |
| 6,103,266 A | 8/2000 | Tapolsky et al. | |
| 6,123,924 A | 9/2000 | Mistry et al. | |
| 6,413,497 B1 | 7/2002 | Weil et al. | |
| 6,475,467 B1 | 11/2002 | Keller et al. | |
| 6,585,958 B1* | 7/2003 | Keller ..................... | A61P 37/08 |
| | | | 424/45 |
| 7,244,742 B2* | 7/2007 | Pieper .................. | A61K 9/0075 |
| | | | 424/45 |
| 8,962,601 B2 | 2/2015 | Lulla et al. | |
| 10,258,568 B2* | 4/2019 | Corr ...................... | A61K 31/573 |
| 10,258,569 B2* | 4/2019 | Corr ...................... | A61K 9/008 |
| 10,792,256 B2* | 10/2020 | Corr ...................... | A61K 9/124 |
| 10,888,546 B2* | 1/2021 | Corr ...................... | A61K 9/008 |
| 2003/0171586 A1 | 9/2003 | Banholzer et al. | |
| 2009/0092559 A1 | 4/2009 | Hoelz et al. | |
| 2014/0308214 A1 | 10/2014 | Malhotra et al. | |
| 2020/0016119 A1* | 1/2020 | Corr ...................... | A61K 47/32 |
| 2020/0016120 A1* | 1/2020 | Corr ...................... | A61K 47/12 |
| 2020/0281874 A1* | 9/2020 | Corr ...................... | A61K 31/573 |

FOREIGN PATENT DOCUMENTS

| | | |
|---|---|---|
| CN | 1296814 | 5/2001 |
| CN | 1389202 | 1/2003 |
| EP | 653204 | 5/1995 |
| EP | 1870090 A2 | 12/2007 |
| WO | WO 91/11173 | 8/1991 |
| WO | WO 92/08447 | 5/1992 |
| WO | WO 96/19198 | 6/1996 |
| WO | WO 99/16422 | 4/1999 |
| WO | WO 99/65460 | 12/1999 |
| WO | WO 01/43722 | 6/2001 |
| WO | WO 2001/047493 A1 | 7/2001 |
| WO | WO 2004/054580 A1 | 7/2004 |
| WO | WO 2005/034911 | 4/2005 |
| WO | WO 2005/034927 | 4/2005 |
| WO | WO 2006/004646 | 1/2006 |
| WO | WO 2007/020204 | 2/2007 |
| WO | WO 2007/121913 A2 | 11/2007 |
| WO | WO 2011/076843 A2 | 6/2011 |
| WO | WO 2012/110770 A2 | 8/2012 |

(Continued)

OTHER PUBLICATIONS

Noakes, Tim "Medical aerosol propellants" Journal of Fluorine Chemistry (2002) 118: 35-45.

*Primary Examiner* — Sean M Basquill

(74) *Attorney, Agent, or Firm* — Brinks Gilson & Lione; Yuezhong Feng

(57) ABSTRACT

A pharmaceutical composition is described. The composition comprises: (i) a drug component comprising at least one salmeterol compound selected from salmeterol and the pharmaceutically acceptable derivatives thereof; and (ii) a propellant component comprising 1,1-difluoroethane (HFA-152a).

16 Claims, No Drawings

(56) References Cited

FOREIGN PATENT DOCUMENTS

| | | |
|---|---|---|
| WO | WO 2012/156711 A1 | 11/2012 |
| WO | WO 2013/054135 A1 | 4/2013 |
| WO | WO 2013/054137 A1 | 4/2013 |
| WO | WO 2014/064410 A2 | 5/2014 |
| WO | WO 2017/093758 A1 | 6/2017 |

* cited by examiner

PHARMACEUTICAL COMPOSITION

This application is a divisional of U.S. patent application Ser. No. 16/334,144, filed Mar. 18, 2019, which is the U.S. National Phase under 35 U.S.C. § 371 of International Application No. PCT/GB2017/052764, filed Sep. 18, 2017, designating the United States and published in English on Mar. 22, 2018, as WO 2018/051133, which claims priority to United Kingdom Application No. 1615914.7, filed Sep. 19, 2016 and to United Kingdom Application No. 1620517.1, filed Dec. 2, 2016, each of which is incorporated by reference in its entirety.

FIELD

The present invention relates to the delivery of drug formulations from a medical device, such as a metered dose inhaler (MDI), using a propellant comprising 1,1-difluoroethane (HFA-152a). More particularly, the present invention relates to pharmaceutical compositions comprising HFA-152a propellant and a drug formulation which is dissolved or suspended in the propellant and to medical devices containing those compositions. The pharmaceutical compositions of the invention are particularly suited for delivery from a pressurised aerosol container using a metered dose inhaler (MDI).

BACKGROUND

MDIs are the most significant type of inhalation drug delivery system and are well known to those skilled in the art. They are designed to deliver, on demand, a discrete and accurate amount of a drug to the respiratory tract of a patient using a liquefied propellant in which the drug is dissolved, suspended or dispersed. The design and operation of MDIs is described in many standard textbooks and in the patent literature. They all comprise a pressurised container that holds the drug formulation, a nozzle and a valve assembly that is capable of dispensing a controlled quantity of the drug through the nozzle when it is activated. The nozzle and valve assembly are typically located in a housing that is equipped with a mouth piece. The drug formulation will comprise a propellant, in which the drug is dissolved, suspended or dispersed, and may contain other materials such as polar excipients, surfactants and preservatives.

In order for a propellant to function satisfactorily in MDIs, it needs to have a number of properties. These include an appropriate boiling point and vapour pressure so that it can be liquefied in a closed container at room temperature but develop a high enough pressure when the MDI is activated to deliver the drug as an atomised formulation even at low ambient temperatures. Further, the propellant should be of low acute and chronic toxicity and have a high cardiac sensitisation threshold. It should have a high degree of chemical stability in contact with the drug, the container and the metallic and non-metallic components of the MDI device, and have a low propensity to extract low molecular weight substances from any elastomeric materials in the MDI device. The propellant should also be capable of maintaining the drug in a homogeneous solution, in a stable suspension or in a stable dispersion for a sufficient time to permit reproducible delivery of the drug in use. When the drug is in suspension in the propellant, the density of the liquid propellant is desirably similar to that of the solid drug in order to avoid rapid sinking or floating of the drug particles in the liquid. Finally, the propellant should not present a significant flammability risk to the patient in use. In particular, it should form a non-flammable or low flammability mixture when mixed with air in the respiratory tract.

Dichlorodifluoromethane (R-12) possesses a suitable combination of properties and was for many years the most widely used MDI propellant, often blended with trichlorofluoromethane (R-11). Due to international concern that fully and partially halogenated chlorofluorocarbons (CFCs), such as dichlorodifluoromethane and trichlorofluoromethane, were damaging the earth's protective ozone layer, many countries entered into an agreement, the Montreal Protocol, stipulating that their manufacture and use should be severely restricted and eventually phased out completely. Dichlorodifluoromethane and trichlorofluoromethane were phased out for refrigeration use in the 1990's, but are still used in small quantities in the MDI sector as a result of an essential use exemption in the Montreal Protocol.

1,1,1,2-tetrafluoroethane (HFA-134a) was introduced as a replacement refrigerant and MDI propellant for R-12. 1,1,1,2,3,3,3-heptafluoropropane (HFA-227ea) was also introduced as a replacement propellant for dichlorotetrafluoroethane (R-114) in the MDI sector and is sometimes used alone or blended with HFA-134a for this application.

Although HFA-134a and HFA-227ea have low ozone depletion potentials (ODPs), they have global warming potentials (GWPs), 1430 and 3220 respectively, which are now considered to be too high by some regulatory bodies, especially for dispersive uses when they are released into the atmosphere.

One industrial area that has received particular attention recently has been the automotive air-conditioning sector where the use of HFA-134a has come under regulatory control as a result of the European Mobile Air Conditioning Directive (2006/40/EC). Industry is developing a number of possible alternatives to HFA-134a in automotive air conditioning and other applications that have a low greenhouse warming potential (GWP) as well as a low ozone depletion potential (ODP). Many of these alternatives include hydrofluoropropenes, especially the tetrafluoropropenes, such as 2,3,3,3-tetrafluoropropene (HFO-1234yf) and 1,3,3,3-tetrafluoropropene (HFO-1234ze).

Although the proposed alternatives to HFA-134a have a low GWP, the toxicological status of many of the components, such as certain of the fluoropropenes, is unclear and they are unlikely to be acceptable for use in the MDI sector for many years, if at all.

Salmeterol and salmeterol xinafoate are long acting beta-2-agonists (LABA) used in the treatment and control of a number of respiratory-related disorders, but particularly asthma and chronic obstructive pulmonary disease (COPD). Both drugs are conveniently delivered using a MDI. Whilst salmeterol treatment is very effective, the performance of salmeterol in many of these therapies may be improved by administration in combination with a corticosteroid, such as the glucocorticoid steroid fluticasone.

There is a need for a salmeterol-based pharmaceutical composition which can be delivered using a MDI and that uses a propellant having a reduced GWP in comparison with HFA-134a and HFA-227ea. There is also a need for a salmeterol-based pharmaceutical composition which exhibits improved stability.

DETAILED DESCRIPTION

We have found that a propellant comprising 1,1-difluoroethane (HFA-152a) can be used to successfully deliver salmeterol-based drug formulations using a MDI. These formulations can exhibit improved chemical stability, particularly where the formulations contain low amounts of water, improved aerosolisation performance for improved drug delivery, good suspension stability, reduced GWP, good compatibility with standard uncoated aluminium cans as well as good compatibility with standard valves and seals.

According to a first aspect of the present invention, there is provided a pharmaceutical composition, e.g. a pharmaceutical suspension or a pharmaceutical solution, said composition comprising:

(i) a drug component comprising at least one salmeterol compound selected from salmeterol and the pharmaceutically acceptable derivatives thereof, especially the pharmaceutically acceptable salts thereof; and (ii) a propellant component comprising 1,1-difluoroethane (HFA-152a).

The pharmaceutical composition of the first aspect of the invention typically contains less than 500 ppm of water based on the total weight of the pharmaceutical composition. The improved chemical stability is observed, in particular, when the pharmaceutical composition contains less than 100 ppm, preferably less than 50 ppm, more preferably less than 10 ppm and particularly less than 5 ppm of water based on the total weight of the pharmaceutical composition. In referring to the water content of the pharmaceutical composition, we are referring to the content of free water in the composition and not any water that happens to be present in any hydrated drug compounds that may be used as part of the drug component. In an especially preferred embodiment, the pharmaceutical composition is water-free. Alternatively, the pharmaceutical composition of the first aspect may contain greater than 0.5 ppm of water, e.g. greater than 1 ppm, but less than the amounts discussed above, as it can in practice be difficult to remove all the water from the composition and then retain it in such a water-free state.

Accordingly a preferred embodiment of the first aspect of the present invention provides a pharmaceutical composition, e.g. a pharmaceutical suspension or a pharmaceutical solution, said composition comprising:

(i) a drug component comprising at least one salmeterol compound selected from salmeterol and the pharmaceutically acceptable derivatives thereof, especially the pharmaceutically acceptable salts thereof; and (ii) a propellant component comprising 1,1-difluoroethane (HFA-152a), wherein the composition contains less than 100 ppm, preferably less than 50 ppm, more preferably less than 10 ppm and especially less than 5 ppm of water based on the total weight of the pharmaceutical composition.

In a preferred embodiment, the pharmaceutical composition of the first aspect of the invention contains less than 1000 ppm, preferably less than 500 ppm, more preferably less than 100 ppm and particularly less than 50 ppm of dissolved oxygen based on the total weight of the pharmaceutical composition. In an especially preferred embodiment, the pharmaceutical composition is oxygen-free. Alternatively, the pharmaceutical composition of the first aspect may contain greater than 0.5 ppm of oxygen, e.g. 1 ppm or greater, but less than the amounts discussed above, as it can in practice be difficult to retain the composition in an oxygen-free state. Low oxygen contents are preferred because they tend to reduce the degradation of the drug compounds resulting in a composition with higher chemical stability.

Accordingly a preferred embodiment of the first aspect of the present invention provides a pharmaceutical composition, e.g. a pharmaceutical suspension or a pharmaceutical solution, said composition comprising:

(i) a drug component comprising at least one salmeterol compound selected from salmeterol and the pharmaceutically acceptable derivatives thereof, especially the pharmaceutically acceptable salts thereof; and (ii) a propellant component comprising 1,1-difluoroethane (HFA-152a), wherein the composition contains less than 1000 ppm, preferably less than 500 ppm, more preferably less than 100 ppm and especially less than 50 ppm of oxygen based on the total weight of the pharmaceutical composition.

The pharmaceutical composition of the present invention is suitable for delivery to the respiratory tract using a metered dose inhaler (MDI).

The at least one salmeterol compound in the pharmaceutical composition of the invention in all aspects and embodiments disclosed herein is preferably in a micronized form. Further, the pharmaceutical composition of the invention in all aspects and embodiments disclosed herein is preferably free of perforated microstructures.

The at least one salmeterol compound may be dispersed or suspended in the propellant. The drug particles in such suspensions preferably have a diameter of less than 100 microns, e.g. less than 50 microns. However, in an alternative embodiment the pharmaceutical compositions of the invention are solutions with the at least one salmeterol compound dissolved in the propellant, e.g. with the assistance of a polar excipient, such as ethanol.

Suitable pharmaceutically acceptable derivatives of salmeterol include, inter alia, pharmaceutically acceptable salts, pharmaceutically acceptable prodrugs, pharmaceutically acceptable solvates, pharmaceutically acceptable hydrates, pharmaceutically acceptable esters, solvates of pharmaceutically acceptable salts, solvates of pharmaceutically acceptable prodrugs, hydrates of pharmaceutically acceptable salts and hydrates of pharmaceutically acceptable prodrugs. A preferred pharmaceutically acceptable derivative of salmeterol is a pharmaceutically acceptable salt thereof, particularly salmeterol xinafoate. In a particularly preferred embodiment, the at least one salmeterol compound in the pharmaceutical composition of the first aspect of the invention is salmeterol or salmeterol xinafoate, especially salmeterol xinafoate.

The amount of the drug component in the pharmaceutical composition of the first aspect of the present invention will typically be in the range of from 0.01 to 2.5 weight % based on the total weight of the pharmaceutical composition. Preferably, the drug component will comprise from 0.01 to 2.0 weight %, more preferably from 0.05 to 2.0 weight % and especially from 0.05 to 1.5 weight % of the total weight of the pharmaceutical composition. The drug component may consist essentially of or consist entirely of the at least one salmeterol compound selected from salmeterol and the pharmaceutically acceptable derivatives thereof. By the term "consists essentially of", we mean that at least 98 weight %, more preferably at least 99 weight % and especially at least 99.9 weight % of the drug component consists of the least one salmeterol compound. Alternatively, the drug component may contain other drugs, such as at least one corticosteroid and/or least one long acting muscarinic antagonist (LAMA).

The propellant component in the pharmaceutical composition of the first aspect of the present invention comprises 1,1-difluoroethane (HFA-152a). Thus, we do not exclude the possibility that the propellant component may include other propellant compounds in addition to the HFA-152a. For example, the propellant component may additionally comprise one or more additional hydrofluorocarbon or to hydrocarbon propellant compounds, e.g. selected from HFA-227ea, HFA-134a, difluoromethane (HFA-32), propane, butane, isobutane and dimethyl ether. The preferred additional propellants are HFA-227ea and HFA-134a.

If an additional propellant compound is included, such as HFA-134a or HFA-227ea, at least 5% by weight, preferably at least 10% by weight and more preferably at least 50% by weight of the propellant component should be HFA-152a. Typically, the HFA-152a will constitute at least 90 weight %, e.g. from 90 to 99 weight %, of the propellant component. Preferably, the HFA-152a will constitute at least 95 weight %, e.g. from 95 to 99 weight %, and more preferably at least 99 weight % of the propellant component.

In a preferred embodiment, the propellant component has a global warming potential (GWP) of less than 250, more preferably less than 200 and still more preferably less than 150.

In an especially preferred embodiment, the propellant component consists entirely of HFA-152a so that the pharmaceutical composition of the invention comprises HFA-152a as the sole propellant. By the term "consists entirely of" we do not, of course, exclude the presence of minor amounts, e.g. up to a few hundred parts per million, of impurities that may be present following the process that is used to make the HFA-152a providing that they do not affect the suitability of the propellant in medical applications. Preferably the HFA-152a propellant will contain no more than 10 ppm, e.g. from 0.5 to 10 ppm, more preferably no more than 5 ppm, e.g. from 1 to 5 ppm, of unsaturated impurities, such as vinyl fluoride, vinyl chloride, vinylidene fluoride and chloro-fluoro ethylene compounds.

The amount of propellant component in the pharmaceutical composition of the invention will vary depending on the amounts of the drugs and other components in the pharmaceutical composition. Typically, the propellant component will comprise from 80.0 to 99.99 weight % of the total weight of the pharmaceutical composition. Preferably, the propellant component will comprise from 90.0 to 99.99 weight %, more preferably from 96.5 to 99.99 weight % and especially from 97.5 to 99.95 weight % of the total weight of the pharmaceutical composition.

In one embodiment, the pharmaceutical composition of the first aspect of the present invention consists essentially of and more preferably consists entirely of the two components (i) and (ii) listed above. By the term "consists essentially of", we mean that at least 98 weight %, more preferably at least 99 weight % and especially at least 99.9 weight % of the pharmaceutical composition consists of the two listed components.

In another embodiment, the pharmaceutical composition of the first aspect of the present invention additionally includes a polar excipient, such as ethanol. Polar excipients have been used previously in pharmaceutical compositions for treating respiratory disorders that are delivered using metered dose inhalers (MDIs). They are also referred to as solvents, co-solvents, carrier solvents and adjuvants. Their inclusion can serve to solubilise the surfactant or the drug in the propellant and/or inhibit deposition of drug particles on the surfaces of the metered dose inhaler that are contacted by the pharmaceutical composition as it passes from the container in which it is stored to the nozzle outlet. They are also used as bulking agents in two-stage filling processes where the drug is mixed with a suitable polar excipient. The most commonly used polar excipient is ethanol. If a polar excipient is used, it will typically be present in an amount of from 0.5 to 10% by weight, preferably in an amount of from 1 to 5% by weight based on the total weight of the pharmaceutical composition.

In one preferred embodiment, the pharmaceutical composition of the present invention is free of polar excipients such as ethanol.

The pharmaceutical composition of the first aspect of the present invention may also include a surfactant component comprising at least one surfactant compound. Where the pharmaceutical composition is a suspension, the surfactant component is preferably not present as a surface coating on the drug particles. Drug particles with such surface coatings are prepared by pre-coating the drug particles with the surfactant component prior to mixing with the propellant component.

Surfactant compounds of the type that have been in use hitherto in pharmaceutical formulations for MDIs may be used in the pharmaceutical compositions of the present invention. Preferred surfactants are selected from polyvinylpyrrolidone, polyethylene glycol surfactants, oleic acid and lecithin. By the term oleic acid, we are not necessarily referring to pure (9Z)-octadec-9-enoic acid. When sold for surfactant use in medical applications, oleic acid is typically a mixture of several fatty acids, with (9Z)-octadec-9-enoic acid being the predominant fatty acid, e.g. present in an amount of at least 65 weight % based on the total weight of the surfactant.

If a surfactant component is included, it is preferably free of fluorinated surfactant compounds. In another embodiment, the surfactant component is free of surfactant compounds selected from $C_{8-16}$ fatty acids or salts, bile salts, phospholipids and alkyl saccharides.

In a preferred embodiment, the surfactant component consists essentially of and still more preferably consists entirely of at least one surfactant compound selected from polyvinylpyrrolidone, polyethylene glycols, oleic acid and lecithin. In a particularly preferred embodiment, the surfactant component consists essentially of and still more preferably consists entirely of at least one surfactant compound selected from polyvinylpyrrolidone and polyethylene glycols. By the term "consists essentially of", we mean that at least 95 weight %, more preferably at least 98 weight % and especially at least 99 weight % of the surfactant component is composed of the listed surfactants.

If a surfactant component is used, it will typically be present in an amount of from 0.1 to 2.5% by weight, preferably in an amount of from 0.2 to 1.5% by weight based on the total weight of the pharmaceutical composition.

The pharmaceutical composition of the invention may also include a long acting muscarinic antagonist (LAMA). Any of the long acting muscarinic antagonists that have been in use hitherto for treating chronic obstructive pulmonary diseases and that can be delivered using a MDI can be used in the pharmaceutical compositions of the present invention. Suitable long acting muscarinic antagonists include umeclidinium, ipratropium, tiotropium, aclidinium and the pharmaceutically acceptable derivatives thereof, especially the pharmaceutically acceptable salts thereof. Preferred compounds include the pharmaceutically acceptable salts of glycopyrrolate (also known as glycopyrronium). Glycopyrrolate is a quaternary ammonium salt. Suitable pharmaceutically acceptable counter ions include, for example, fluoride, chloride, bromide, iodide, nitrate, sulfate, phosphate, formate, acetate, trifluoroacetate, propionate, butyrate, lactate, citrate, tartrate, malate, maleate, succinate, benzoate, p-chlorobenzoate, diphenyl-acetate or triphenylacetate, o-hydroxybenzoate, p-hydroxybenzoate, 1-hydroxynaphthalene-2-carboxylate, 3-hydroxynaphthalene-2-carboxylate, methanesulfonate and benzenesulfonate. A preferred compound is the bromide salt of glycopyrrolate also known as glycopyrronium bromide.

According to a second aspect of the present invention, there is provided a pharmaceutical composition, e.g. a pharmaceutical suspension or a pharmaceutical solution, said composition comprising:
(i) a drug component comprising at least one salmeterol compound selected from salmeterol and the pharmaceutically acceptable derivatives thereof, especially the pharmaceutically acceptable salts thereof and at least one long acting muscarinic antagonist, particularly at least one pharmaceutically acceptable salt of glycopyrrolate; and
(ii) a propellant component comprising 1,1-difluoroethane (HFA-152a).

The pharmaceutical composition of the second aspect of the invention typically contains less than 500 ppm of water based on the total weight of the pharmaceutical composition. Preferably, the pharmaceutical composition of the second aspect of the invention contains less than 100 ppm, more preferably less than 50 ppm, particularly less than 10 ppm and especially less than 5 ppm of water based on the total weight of the pharmaceutical composition. It has been found that small amounts of water alongside the use of HFA-152a as the propellant can result in a pharmaceutical composition with improved chemical stability. In referring to the water content of the pharmaceutical composition, we are referring to the content of free water in the composition and not any water that happens to be present in any hydrated drug compounds that may be used as part of the drug component. In an especially preferred embodiment, the pharmaceutical composition of the second aspect of the present invention is water-free. Alternatively, the pharmaceutical composition of the second aspect may contain greater than 0.5 ppm of water, e.g. greater than 1 ppm, but less than the amounts discussed above, as it can in practice be difficult to remove all the water from the composition and then retain it in such a water-free state.

In a preferred embodiment, the pharmaceutical composition of the second aspect of the invention contains less than 1000 ppm, preferably less than 500 ppm, more preferably less than 100 ppm and particularly less than 50 ppm of dissolved oxygen based on the total weight of the pharmaceutical composition. In an especially preferred embodiment, the pharmaceutical composition is oxygen-free. Alternatively, the pharmaceutical composition of the second aspect may contain greater than 0.5 ppm of oxygen, e.g. 1 ppm or greater, but less than the amounts discussed above, as it can in practice be difficult to retain the composition in an oxygen-free state. Low oxygen contents are preferred because they tend to reduce the degradation of the drug compounds resulting in a composition with higher chemical stability.

Suitable and preferred salmeterol compounds are as discussed above for the pharmaceutical composition of the first aspect of the present invention.

Typical and preferred amounts of the drug component and the propellant component in the pharmaceutical composition of the second aspect of the present invention and suitable, typical and preferred compositions for the propellant component are as discussed above for the pharmaceutical composition of the first aspect of the invention. The drug component may consist essentially of or consist entirely of the at least one salmeterol compound and the at least one long acting muscarinic antagonist. By the term "consists essentially of", we mean that at least 98 weight %, more preferably at least 99 weight % and especially at least 99.9 weight % of the drug component consists of the at least one salmeterol compound and the at least one long acting muscarinic antagonist.

In one embodiment, the pharmaceutical composition of the second aspect of the present invention consists essentially of and more preferably consists entirely of the two components (i) and (ii) listed above. By the term "consists essentially of", we mean that at least 98 weight %, more preferably at least 99 weight % and especially at least 99.9 weight % of the pharmaceutical composition consists of the two listed components.

In another embodiment, the pharmaceutical composition of the second aspect of the invention may contain one or both of a polar excipient and a surfactant component as discussed above for the pharmaceutical composition of the first aspect of the invention. Suitable and preferred polar excipients and surfactants are as discussed above for the pharmaceutical composition of the first aspect of the invention. Typical and preferred amounts of the polar excipient and the surfactant component are as discussed above for the pharmaceutical composition of the first aspect of the invention.

In an especially preferred embodiment of the second aspect of the invention, the drug component comprises at least one salmeterol compound selected from salmeterol and salmeterol xinafoate and at least one pharmaceutically acceptable salt of glycopyrrolate, especially glycopyrronium bromide. Preferably, the at least one selected salmeterol compound and the at least one selected pharmaceutically acceptable salt of glycopyrrolate are the only pharmaceutical actives in the pharmaceutical composition of the second aspect of the invention.

The pharmaceutical composition of the invention may also include a corticosteroid. Any of the corticosteroids that have been in use hitherto for treating asthma and chronic obstructive pulmonary diseases and that can be delivered using a MDI can be used in the pharmaceutical compositions of the present invention. Suitable corticosteroids include budesonide, mometasone, beclomethasone and fluticasone as well as their pharmaceutically acceptable derivatives, such as their pharmaceutically acceptable salts and esters. Preferred compounds include fluticasone and fluticasone propionate.

Accordingly, a third aspect of the present invention provides a pharmaceutical composition, e.g. a pharmaceutical suspension or a pharmaceutical solution, said composition comprising:
(i) a drug component comprising at least one salmeterol compound selected from salmeterol and the pharmaceutically acceptable derivatives thereof, especially the pharmaceutically acceptable salts thereof and at least one corticosteroid, particularly at least one corticosteroid selected from fluticasone, budesonide, mometasone and beclomethasone and the pharmaceutically acceptable derivatives thereof, especially fluticasone and fluticasone propionate; and
(ii) a propellant component comprising 1,1-difluoroethane (HFA-152a).

The pharmaceutical composition of the third aspect of the invention typically contains less than 500 ppm of water based on the total weight of the pharmaceutical composition. Preferably, the pharmaceutical composition of the third aspect of the invention contains less than 100 ppm, more preferably less than 50 ppm, particularly less than 10 ppm and especially less than 5 ppm of water based on the total weight of the pharmaceutical composition. It has been found that small amounts of water alongside the use of HFA-152a as the propellant can result in a pharmaceutical composition with improved chemical stability. In referring to the water content of the pharmaceutical composition, we are referring to the content of free water in the composition and not any water that happens to be present in any hydrated drug compounds that may be used as part of the drug component. In an especially preferred embodiment, the pharmaceutical composition of the third aspect of the present invention is water-free. Alternatively, the pharmaceutical composition of the third aspect may contain greater than 0.5 ppm of water, e.g. greater than 1 ppm, but less than the amounts discussed above, as it can in practice be difficult to remove all the water from the composition and then retain it in such a water-free state.

In a preferred embodiment, the pharmaceutical composition of the third aspect of the invention contains less than 1000 ppm, preferably less than 500 ppm, more preferably less than 100 ppm and particularly less than 50 ppm of dissolved oxygen based on the total weight of the pharmaceutical composition. In an especially preferred embodiment, the pharmaceutical composition is oxygen-free. Alternatively, the pharmaceutical composition of the third aspect may contain greater than 0.5 ppm of oxygen, e.g. 1 ppm or greater, but less than the amounts discussed above, as it can in practice be difficult to retain the composition in an oxygen-free state. Low oxygen contents are preferred because they tend to reduce the degradation of the drug compounds resulting in a composition with higher chemical stability.

Suitable and preferred salmeterol compounds are as discussed above for the pharmaceutical composition of the first aspect of the present invention.

Typical and preferred amounts of the drug component and the propellant component in the pharmaceutical composition of the third aspect of the present invention and suitable, typical and preferred compositions for the propellant component are as discussed above for the pharmaceutical composition of the first aspect of the invention. The drug component may consist essentially of or consist entirely of the at least one salmeterol compound and the at least one corticosteroid. By the term "consists essentially of", we mean that at least 98 weight %, more preferably at least 99 weight % and especially at least 99.9 weight % of the drug component consists of the at least one salmeterol compound and the at least one corticosteroid.

In one embodiment, the pharmaceutical composition of the third aspect of the present invention consists essentially of and more preferably consists entirely of the two components (i) and (ii) listed above. By the term "consists essentially of", we mean that at least 98 weight %, more preferably at least 99 weight % and especially at least 99.9 weight % of the pharmaceutical composition consists of the two listed components.

In another embodiment, the pharmaceutical composition of the third aspect of the invention may contain one or both of a polar excipient and a surfactant component as discussed above for the pharmaceutical composition of the first aspect of the invention. Suitable and preferred polar excipients and surfactants are as discussed above for the pharmaceutical composition of the first aspect of the invention. Typical and preferred amounts of the polar excipient and the surfactant component are as discussed above for the pharmaceutical composition of the first aspect of the invention.

In an especially preferred embodiment of the third aspect of the invention, the drug component comprises at least one salmeterol compound selected from salmeterol and salmeterol xinafoate and fluticasone propionate. Preferably, the at least one selected salmeterol compound and the fluticasone propionate are the only pharmaceutical actives in the pharmaceutical composition of the third aspect of the invention.

The pharmaceutical composition of the invention may also include a long acting muscarinic antagonist (LAMA) and a corticosteroid. Any of the long acting muscarinic antagonists and corticosteroids that have been in use hitherto for treating asthma and chronic obstructive pulmonary diseases and that can be delivered using a MDI can be used in the pharmaceutical compositions of the present invention. Suitable and preferred long acting muscarinic antagonists are as discussed above for the second aspect of the invention. Suitable and preferred corticosteroids are as discussed above for the third aspect of the present invention.

Accordingly, a fourth aspect of the present invention provides a pharmaceutical composition, e.g. a pharmaceutical suspension or a pharmaceutical solution, said composition comprising:

(i) a drug component comprising at least one salmeterol compound selected from salmeterol and the pharmaceutically acceptable derivatives thereof, especially the pharmaceutically acceptable salts thereof, at least one long acting muscarinic antagonist, particularly at least one pharmaceutically acceptable salt of glycopyrrolate, and at least one corticosteroid, particularly at least one corticosteroid selected from fluticasone, budesonide, mometasone and beclomethasone and the pharmaceutically acceptable derivatives thereof, especially fluticasone and fluticasone propionate; and (ii) a propellant component comprising 1,1-difluoroethane (HFA-152a).

The pharmaceutical composition of the fourth aspect of the invention typically contains less than 500 ppm of water based on the total weight of the pharmaceutical composition. Preferably, the pharmaceutical composition of the fourth aspect of the present invention contains less than 100 ppm, more preferably less than 50 ppm, particularly less than 10 ppm and especially less than 5 ppm of water based on the total weight of the pharmaceutical composition. It has been found that small amounts of water alongside the use of HFA-152a as the propellant can result in a pharmaceutical composition with improved chemical stability. In referring to the water content of the pharmaceutical composition, we are referring to the content of free water in the composition and not any water that happens to be present in any hydrated drug compounds that may be used as part of the drug component. In an especially preferred embodiment, the pharmaceutical composition of the fourth aspect of the present invention is water-free. Alternatively, the pharmaceutical composition of the fourth aspect may contain greater than 0.5 ppm of water, e.g. greater than 1 ppm, but less than the amounts discussed above, as it can in practice be difficult to remove all the water from the composition and then retain it in such a water-free state.

In a preferred embodiment, the pharmaceutical composition of the fourth aspect of the invention contains less than 1000 ppm, preferably less than 500 ppm, more preferably less than 100 ppm and particularly less than 50 ppm of dissolved oxygen based on the total weight of the pharmaceutical composition. In an especially preferred embodiment, the pharmaceutical composition is oxygen-free. Alternatively, the pharmaceutical composition of the fourth aspect may contain greater than 0.5 ppm of oxygen, e.g. 1 ppm or greater, but less than the amounts discussed above, as it can in practice be difficult to retain the composition in an oxygen-free state. Low oxygen contents are preferred because they tend to reduce the degradation of the drug compounds resulting in a composition with higher chemical stability.

Suitable and preferred salmeterol compounds are as discussed above for the pharmaceutical composition of the first aspect of the present invention.

Typical and preferred amounts of the drug component and the propellant component in the pharmaceutical composition of the fourth aspect of the present invention and suitable, typical and preferred compositions for the propellant component are as discussed above for the pharmaceutical composition of the first aspect of the invention. The drug component may consist essentially of or consist entirely of the at least one salmeterol compound, the at least one long acting muscarinic antagonist (LAMA) and the at least one corticosteroid. By the term "consists essentially of", we mean that at least 98 weight %, more preferably at least 99 weight % and especially at least 99.9 weight % of the drug component consists of the at least one salmeterol compound, the at least one long acting muscarinic antagonist (LAMA) and the at least one corticosteroid.

In one embodiment, the pharmaceutical composition of the fourth aspect of the present invention consists essentially of and more preferably consists entirely of the two components (i) and (ii) listed above. By the term "consists essentially of", we mean that at least 98 weight %, more preferably at least 99 weight % and especially at least 99.9 weight % of the pharmaceutical composition consists of the two listed components.

In another embodiment, the pharmaceutical composition of the fourth aspect of the invention may contain one or both of a polar excipient and a surfactant component as discussed above for the pharmaceutical composition of the first aspect of the invention. Suitable and preferred polar excipients and surfactants are as discussed above for the pharmaceutical composition of the first aspect of the invention. Typical and preferred amounts of the polar excipient and the surfactant component are as discussed above for the pharmaceutical composition of the first aspect of the invention.

In an especially preferred embodiment of the fourth aspect of the invention, the drug component comprises at least one salmeterol compound selected from salmeterol and salmeterol xinafoate, at least one pharmaceutically acceptable salt of glycopyrrolate, especially glycopyrronium bromide, and fluticasone propionate. Preferably, the at least one selected salmeterol compound, the at least one pharmaceutically acceptable salt of glycopyrrolate and the fluticasone propionate are the only pharmaceutical actives in the pharmaceutical composition of the fourth aspect of the invention.

It has been found that the use of propellants comprising 1,1-difluoroethane (HFA-152a) in pharmaceutical compositions containing a salmeterol compound, such as salmeterol xinafoate, and the propellant can unexpectedly improve the chemical stability of the salmeterol compound compared to the stability it exhibits in formulations containing either HFA-134a or HFA-227ea as the propellant.

Accordingly, in a fifth aspect of the present invention there is provided a method of improving the stability of a pharmaceutical composition comprising a propellant component and a drug component comprising at least one salmeterol compound selected from salmeterol and the pharmaceutically acceptable derivatives thereof, said method comprising using a propellant component comprising 1,1-difluoroethane (HFA-152a).

The pharmaceutical composition in the stabilisation method of the fifth aspect of the present invention may be a suspension or a solution.

The improved chemical stability can result, in particular, when the pharmaceutical composition contains less than 500 ppm, preferably less than 100 ppm, more preferably less than 50 ppm, still more preferably less than 10 ppm and particularly less than 5 ppm of water based on the total weight of the pharmaceutical composition. In referring to the water content of the pharmaceutical composition, we are referring to the content of free water in the composition and not any water that happens to be present in any hydrated drug compounds that may be used as part of the drug component. In an especially preferred embodiment, the pharmaceutical composition is water-free. Alternatively, the pharmaceutical composition recited in the fifth aspect of the present invention may contain greater than 0.5 ppm of water, e.g. greater than 1 ppm, but less than the amounts discussed above, as it can in practice be difficult to remove all the water from the composition and then retain it in such a water-free state.

Accordingly, in a preferred embodiment of the fifth aspect of the present invention there is provided a method of improving the stability of a pharmaceutical composition comprising a propellant component and a drug component comprising at least one salmeterol compound selected from salmeterol and the pharmaceutically acceptable derivatives thereof, said method comprising using a propellant component comprising 1,1-difluoroethane (HFA-152a) and selecting the components and conditions for the preparation of the pharmaceutical composition to maintain the water content of the pharmaceutical composition below 100 ppm, preferably below 50 ppm, more preferably below 10 ppm and particularly below 5 ppm based on the total weight of the pharmaceutical composition.

In practice, preparing a pharmaceutical composition with the low water levels recited above involves using a propellant component with a suitably low water content, as it is usually the largest mass item in the finished device, and then preparing the pharmaceutical composition under suitably dry conditions, e.g. in a dry nitrogen atmosphere. Preparing pharmaceutical compositions under dry conditions is well known and the techniques involved are well understood by those skilled in the art. Other steps to obtain a low water content in the finished device include drying and storing the can and valve components in a moisture-controlled atmosphere, e.g. dry nitrogen or air, prior to and during device assembly. If the pharmaceutical composition contains a significant amount of ethanol, then it may also be important to control the water content of the ethanol as well as the propellant, e.g. by drying to reduce the water content to suitably low levels. Suitable drying techniques are well known to those skilled in the art and include the use of a molecular sieve or other inorganic desiccant and membrane drying processes.

In the stabilisation method of the fifth aspect of the present invention suitable and preferred salmeterol compounds and derivatives thereof are as described above for the pharmaceutical composition of the first aspect of the present invention. In addition, typical and preferred amounts of the drug component and the propellant component in the stabilisation method of the fifth aspect of the present invention and suitable, typical and preferred compositions for the propellant component are as discussed above for the pharmaceutical composition of the first aspect of the invention.

The drug component in the stabilisation method of the fifth aspect of the present invention may consist essentially of or consist entirely of the at least one salmeterol compound selected from salmeterol and the pharmaceutically acceptable derivatives thereof. By the term "consists essentially of", we mean that at least 98 weight %, more preferably at least 99 weight % and especially at least 99.9 weight % of the drug component consists of the least one salmeterol compound. Alternatively, the drug component may additionally comprise at least one long acting muscarinic antagonist and/or at least one corticosteroid. When a long acting muscarinic antagonist and/or a corticosteroid are included, suitable and preferred long acting muscarinic antagonists and suitable and preferred corticosteroids are as described above for the pharmaceutical compositions of the second and third aspects of the present invention.

In one embodiment, the pharmaceutical composition in the fifth aspect of the present invention consists essentially of and more preferably consists entirely of the drug component and the propellant component as defined above. By the term "consists essentially of", we mean that at least 98 weight %, more preferably at least 99 weight % and especially at least 99.9 weight % of the pharmaceutical composition consists of the two components.

In an alternative embodiment, the pharmaceutical composition in the fifth aspect of the invention may contain one or both of a polar excipient and a surfactant component as discussed above for the pharmaceutical composition of the first aspect of the invention. Suitable and preferred polar excipients and surfactants are as discussed above for the pharmaceutical composition of the first aspect of the invention. Typical and preferred amounts of the polar excipient and the surfactant component are as discussed above for the pharmaceutical composition of the first aspect of the invention.

In one preferred stabilisation method, the resulting pharmaceutical composition after storage at 40° C. and 75% relative humidity for 6 months will produce less than 0.4% by weight and preferably less than 0.36% by weight of impurities from the degradation of the at least one salmeterol compound based on the total weight of the at least one salmeterol compound and the impurities.

In another preferred stabilisation method in which the pharmaceutical composition also comprises at least one corticosteroid and/or at least one long acting muscarinic antagonist, the resulting pharmaceutical composition after storage at 40° C. and 75% relative humidity for 6 months will produce less than 0.4% by weight and preferably less than 0.36% by weight of impurities from the degradation of the at least one salmeterol compound based on the total weight of the at least one salmeterol compound and the impurities.

In yet another preferred stabilisation method, at least 97.5% by weight, preferably at least 98.0% by weight and more preferably at least 98.5% by weight of the at least one salmeterol compound that is contained originally in the pharmaceutical composition immediately following preparation will be present in the composition after storage at 40° C. and 75% relative humidity for 6 months.

In still another preferred stabilisation method in which the pharmaceutical composition also comprises at least one corticosteroid and/or at least one long acting muscarinic antagonist, at least 97.5% by weight, preferably at least 98.0% by weight and more preferably at least 98.5% by weight of the at least one salmeterol compound that is contained originally in the pharmaceutical composition immediately following preparation will be present in the composition after storage at 40° C. and 75% relative humidity for 6 months.

In a further preferred stabilisation method, at least 97.5%, preferably at least 98.0% and more preferably at least 98.5% of the original pharmaceutical activity of the composition is retained after storage at 40° C. and 75% relative humidity for 6 months.

One preferred pharmaceutical composition of the first, second, third and fourth aspects of the present invention will produce less than 0.4% by weight and preferably less than 0.36% by weight of total impurities from the degradation of the at least one salmeterol compound after storage at 40° C. and 75% relative humidity for 6 months.

The weight % of impurities indicated above are based on the total weight of the at least one salmeterol compound and the impurities.

In a further preferred pharmaceutical composition of the first, second, third and fourth aspects of the present invention at least 97.5% by weight, preferably at least 98.0% by weight and more preferably at least 98.5% by weight of the at least one salmeterol compound that is contained originally in the pharmaceutical composition of the invention immediately following preparation will be present in the composition after storage at 40° C. and 75% relative humidity for 6 months.

In yet another preferred pharmaceutical composition of the first, second, third and fourth aspects of the present invention at least 97.5%, preferably at least 98.0% and more preferably at least 98.5% of the original pharmaceutical activity of the pharmaceutical composition of the invention is retained after storage at 40° C. and 75% relative humidity for 6 months.

In referring to the storage of the pharmaceutical compositions in the above 30 described stabilisation methods, we are referring, in particular, to the storage of those compositions in uncoated aluminium containers. Similarly, in referring to the storage of the above described pharmaceutical compositions, we are referring, in particular, to their storage in uncoated aluminium containers.

It has been found that the use of propellants comprising 1,1-difluoroethane (HFA-152a) in pharmaceutical compositions containing a salmeterol compound, such as salmeterol xinafoate, and the propellant that are designed to be delivered using a metered dose inhaler can unexpectedly improve the aerosolization performance of the pharmaceutical composition when that composition is delivered from the metered dose inhaler compared to the performance that is observed when either HFA-134a or HFA-227ea is used as the propellant. In particular, the fine particle fraction of the salmeterol compound in the emitted dose typically comprises at least 40 weight %, preferably at least 42.5 weight % and more preferably at least 45 weight % of the emitted dose of the salmeterol compound. We are referring here, in particular, to the emitted dose that is observed immediately after the pharmaceutical composition has been filled into a MDI canister and prior to any long term storage.

Accordingly, in a sixth aspect of the present invention there is provided a method of improving the aerosolization performance of a pharmaceutical composition comprising a propellant component and a drug component comprising at least one salmeterol compound selected from salmeterol and the pharmaceutically acceptable derivatives thereof, said method comprising using a propellant component comprising 1,1-difluoroethane (HFA-152a).

The pharmaceutical composition in the method of the sixth aspect of the present invention may be a suspension or a solution.

In a preferred embodiment of the sixth aspect of the present invention there is provided a method of improving the aerosolization performance of a pharmaceutical composition comprising a propellant component and a drug component comprising at least one salmeterol compound selected from salmeterol and the pharmaceutically acceptable derivatives thereof, said method comprising using a propellant component comprising 1,1-difluoroethane (HFA-152a) and providing a pharmaceutical composition which when delivered from a metered dose inhaler yields a fine particle fraction of the at least one salmeterol compound which is at least 40 weight %, preferably at least 42.5 weight % and more preferably at least 45 weight % of the emitted dose of the at least one salmeterol compound.

Increasing the fine particle fraction of the emitted dose is highly beneficial, because it is the fine drug particles that are able to penetrate into the deep bronchiole passages and the alveolar passages of the lung to maximise relief from the effects of an asthma attack or COPD.

The fine particle fraction is a widely recognised term in the art. It is a measure of the mass fraction of emitted aerosol particles having a diameter below 5 μm which is generally accepted as being the most desirable particle size range for effective alveolar drug delivery.

In the method of the sixth aspect of the present invention suitable and preferred to salmeterol compounds are as described above for the pharmaceutical composition of the first aspect of the present invention. In addition, typical and preferred amounts of the drug component and the propellant component in the method of the sixth aspect of the present invention and suitable, typical and preferred compositions for the propellant component are as discussed above for the pharmaceutical composition of the first aspect of the invention.

The drug component in the method of the sixth aspect of the present invention may consist essentially of or consist entirely of the at least one salmeterol compound, such as salmeterol and/or salmeterol xinafoate. By the term "consists essentially of", we mean that at least 98 weight %, more preferably at least 99 weight % and especially at least 99.9 weight % of the drug component consists of the least one salmeterol compound. Alternatively, the drug component may additionally comprise at least one long acting muscarinic antagonist and/or at least one corticosteroid. When a long acting muscarinic antagonist and/or corticosteroid are included, suitable and preferred long acting muscarinic antagonists and suitable and preferred corticosteroids are as described above for the pharmaceutical compositions of the second and third aspects of the present invention.

In one embodiment, the pharmaceutical composition in the sixth aspect of the present invention consists essentially of and more preferably consists entirely of the drug component and the propellant component as defined above. By the term "consists essentially of", we mean that at least 98 weight %, more preferably at least 99 weight % and especially at least 99.9 weight % of the pharmaceutical composition consists of the two components.

In an alternative embodiment, the pharmaceutical composition in the sixth aspect of the invention may contain one or both of a polar excipient and a surfactant component as discussed above for the pharmaceutical composition of the first aspect of the invention. Suitable and preferred polar excipients and surfactants are as discussed above for the pharmaceutical composition of the first aspect of the invention. Typical and preferred amounts of the polar excipient and the surfactant component are as discussed above for the pharmaceutical composition of the first aspect of the invention.

In a particularly preferred embodiment of the sixth aspect of the present invention, the drug component comprises salmeterol xinafoate and fluticasone propionate and the fine particle fraction of salmeterol xinafoate in the emitted dose when the pharmaceutical composition is delivered from a metered dose inhaler is at least 40 weight %, preferably at least 42.5 weight % and more preferably at least 45 weight 15% of the emitted dose of the salmeterol xinafoate. In addition, the fine particle fraction of fluticasone propionate in the emitted dose when the pharmaceutical composition is delivered from a metered dose inhaler is preferably at least 33 weight %, more preferably at least 36 weight % and still more preferably at least 39 weight % of the emitted dose of the fluticasone propionate.

The pharmaceutical compositions of the invention find particular utility in the delivery of the salmeterol compounds, and where included the corticosteroid and long acting muscarinic antagonist compounds, from a pressurised aerosol container, e.g. using a metered dose inhaler (MDI). For this application, the pharmaceutical compositions are contained in the pressurised aerosol container and the HFA-152a propellant functions to deliver the drug as a fine aerosol spray.

The pharmaceutical compositions of the invention may comprise one or more other additives of the type that are conventionally used in drug formulations for pressurised MDIs, such as valve lubricants. Where other additives are included in the pharmaceutical compositions, they are normally used in amounts that are conventional in the art.

The pharmaceutical compositions of the invention are normally stored in a pressurised container or canister which is to be used in association with a medication delivery device. When so stored, the pharmaceutical compositions are normally a liquid. In a preferred embodiment, the pressurised container is designed for use in a metered dose inhaler (MDI). In a particularly preferred embodiment, the pressurised container is a coated aluminium can or an uncoated aluminium can, especially the latter.

Accordingly, a seventh aspect of the present invention provides a pressurised container holding the pharmaceutical composition of the first, second, third or fourth aspect of the present invention. In an eighth aspect, the present invention provides a medication delivery device, especially a metered dose inhaler, having a pressurised container holding the pharmaceutical composition of the first, second, third or fourth aspect of the present invention.

The metered dose inhaler typically comprises a nozzle and valve assembly that is crimped to a container holding the pharmaceutical composition to be dispensed. An elastomeric gasket is used to provide a seal between the container and the nozzle/valve assembly. Preferred elastomeric gasket materials are EPDM, chlorobutyl, bromobutyl and cycloolefin copolymer rubbers as these can exhibit good compatibility with HFA-152a and also provide a good barrier to prevent or limit HFA-152a permeating from the container.

The pharmaceutical compositions of the present invention are for use in medicine for treating a patient suffering or likely to suffer from a respiratory disorder and especially asthma or a chronic obstructive pulmonary disease.

Accordingly, the present invention also provides a method for treating a patient suffering or likely to suffer from a respiratory disorder, especially asthma or a chronic obstructive pulmonary disease, which comprises administering to the patient a therapeutically or prophylactically effective amount of a pharmaceutical composition as discussed above. The pharmaceutical composition is preferably delivered to the patient using a MDI.

The pharmaceutical compositions of the invention can be prepared and the MDI devices filled using techniques that are standard in the art, such as pressure filling and cold filling. For example, the pharmaceutical compositions can be prepared by a simple blending operation in which the at least one salmeterol compound, optionally the at least one corticosteroid and/or the at least one long acting muscarinic antagonist, optionally the surfactant component and the HFA-152a-containing propellant are mixed together in the required proportions in a suitable mixing vessel. Mixing can be promoted by stirring as is common in the art. Conveniently, the HFA-152a-containing propellant is liquefied to aid mixing. If the pharmaceutical composition is made in a separate mixing vessel, it can then be transferred to pressurised containers for storage, such as pressurised containers that are used as part of medication delivery devices and especially MDIs.

The pharmaceutical compositions of the invention can also be prepared within the confines of a pressurised container, such as an aerosol canister or vial, from which the compositions are ultimately released as an aerosol spray using a medication delivery device, such as a MDI. In this method, a weighed amount of the at least one salmeterol compound and optionally the at least one corticosteroid and/or the at least one long acting muscarinic antagonist, is introduced into the open container. A valve is then crimped onto the container and the HFA-152a-containing propellant component, in liquid form, introduced through the valve into the container under pressure, optionally after first evacuating the container through the valve. The surfactant component, if included, can be mixed with the drug(s) or, alternatively, introduced into the container after the valve has been fitted, either alone or as a premix with the propellant component. The whole mixture can then be treated to disperse the drugs in the propellant/surfactant mixture, e.g. by vigorous shaking or using an ultrasonic bath. Suitable containers may be made of plastics, metal, e.g. aluminium, or glass. Preferred containers are made of metal, especially aluminium which may be coated or uncoated. Uncoated aluminium containers are especially preferred.

The container may be filled with enough of the pharmaceutical composition to provide for a plurality of dosages. The pressurized aerosol canisters that are used in MDIs typically contain 50 to 150 individual dosages.

The present invention also provides a method of reducing the global warming potential (GWP) of a pharmaceutical composition comprising a drug component comprising at least one salmeterol compound selected from salmeterol and the pharmaceutically acceptable derivatives thereof, especially the pharmaceutically acceptable salts thereof and a propellant component, said method comprising using a propellant component comprising 1,1-difluoroethane (HFA-152a). This method is applicable to the preparation of all the pharmaceutical compositions disclosed herein in all their aspects and embodiments.

Preferably, at least 90 weight %, more preferably at least 95 weight % and still more preferably at least 99 weight % of the propellant component used is HFA-152a. In an especially preferred embodiment, the propellant component used is entirely HFA-152a.

The propellant component that is used will preferably have a global warming potential (GWP) of less than 250, more preferably less than 200 and still more preferably less than 150.

The present invention is now illustrated but not limited by the following examples.

Example 1

A number of experiments were conducted to investigate the in vitro aerosolization performance of combination drug formulations of salmeterol xinafoate and fluticasone propionate in metered dose inhalers (MDIs) using either HFA-134a or HFA-152a as the propellant.

Pharmaceutical formulations of salmeterol xinafoate and fluticasone propionate were prepared in either HFA-134a or HFA-152a (Mexichem, UK). The drugs were weighed directly into standard uncoated 14 ml aluminium canisters (C128, 25 Presspart, Blackburn, UK). The canisters were then crimped with a 50 µL valve (Bespak, Kings Lynn, UK) following which the propellant was filled into the canisters through the valve using a manual Pamasol crimper/filler (Pamasol, Switzerland). Finally, the canisters were sonicated for 20 minutes to aid dispersion of the drug in the suspension. The nominal dose of salmeterol xinafoate was 25 µg and the nominal dose of fluticasone propionate was 125 µg.

High performance liquid chromatography (HPLC) was used to determine drug content following aerosolization studies (see below). A 100 mm×4.6 mm Ascentis Express $C_{18}$ column with a 2.7 µm particle size was used for the analysis. The 35 column was coupled to a UV detector operating at a wavelength of 235 and 252 nm. The autosampler was operated at ambient temperature and 100 µl samples were injected into the column for the analyses. The chromatographic conditions are shown in Table 1 below.

TABLE 1

| Drug | Pump Flow Rate (ml · min$^{-1}$) | Mobile Phase | UV Wavelength (nm) | Column Temperature (° C.) |
|---|---|---|---|---|
| Fluticasone Propionate | 1.5 | Methanol, Acetonitrile and Water 45/35/20% v/v | 235 | 40 |
| Salmeterol Xinafoate | 1.5 | Methanol, Acetonitrile and Water 45/35/20% v/v | 252 | 40 |

The in vitro aerosolization performance of the formulations was studied using a Next Generation Impactor (NGI, Copley Scientific, Nottingham UK), which was connected to a vacuum pump (GE Motors, N.J., USA). Prior to testing, the cups of the NGI system were coated with 1% v/v silicone oil in hexane to eliminate particle bounce. For each experiment, three actuations of the valve were discharged into the NGI at 30 L·min$^{-1}$ as per pharmacopeia guidelines. Following aerosolization, the NGI apparatus was dismantled and the actuator and each part of the NGI was washed down into known volumes of the HPLC mobile phase. The mass of drug deposited on each part of the NGI was determined by HPLC using the methodology described above. This protocol was repeated three times for each canister, following which, the fine particle dose (FPD) and fine particle fraction of the emitted dose ($FPF_{ED}$) were determined. The results are shown in Tables 2 and 3 below.

TABLE 2

In vitro aerosolization performance of combination MDI formulations of salmeterol xinafoate and fluticasone propionate in HFA-134a as characterised by the emitted dose, fine particle dose, fine particle fraction of the emitted dose ($FPF_{ED}$ (%)), mass median aerodynamic diameter (MMAD) and geometric standard deviation (GSD).

| Formulation | Emitted Dose (μg ± S.D.) | Fine particle Dose (μg ± S.D.) | $FPF_{ED}$ (%) | MMAD ± GSD |
|---|---|---|---|---|
| Fluticasone Propionate | 101.7 ± 8.7 | 31.6 ± 3.3 | 31.0 | 3.8 ± 2.5 |
| Salmeterol Xinafoate | 22.9 ± 1.3 | 8.4 ± 0.3 | 36.7 | 2.6 ± 2.6 |

TABLE 3

In vitro aerosolization performance of combination MDI formulations of salmeterol xinafoate and fluticasone propionate in HFA-152a as characterised by the emitted dose, fine particle dose, fine particle fraction of the emitted dose ($FPF_{ED}$ (%)), mass median aerodynamic diameter (MMAD) and geometric standard deviation (GSD).

| Formulation | Emitted Dose (μg ± S.D.) | Fine particle Dose (μg ± S.D.) | $FPF_{ED}$ (%) | MMAD ± GSD |
|---|---|---|---|---|
| Fluticasone Propionate | 108.7 ± 1.1 | 43.5 ± 3.4 | 40.0 | 2.9 ± 2.1 |
| Salmeterol Xinafoate | 18.8 ± 1.6 | 8.9 ± 0.8 | 47.2 | 2.4 ± 2.1 |

It is evident from the data presented in Tables 2 and 3 above that the fine particle fractions of the emitted doses upon aerosolization were significantly better when HFA-152a was used as the propellant for both salmeterol xinafoate and fluticasone propionate.

Example 2

The stability of salmeterol xinafoate and fluticasone propionate in HFA-134a and HFA-152a was investigated at time zero (T=0) and after storage, valve down, for 1 month (T=1M), 3 months (T=3M) and 6 months (T=6M) at 40° C. and 75% relative humidity (RH) and at 25° C. and 60% relative humidity (RH) in uncoated aluminium cans.

The drug formulations were prepared as described in Example 1 and analysed using HPLC following the stability studies. A 100 mm×4.6 mm Ascentis Express $C_{18}$ column with a 2.7 μm particle size was used for the analysis. The column was coupled to a UV detector operating at a wavelength of 214 nm. The autosampler was operated at ambient temperature and 100 μl samples were injected into the column for the analyses. The chromatographic conditions are shown in Table 4 below.

TABLE 4

| Drug | Pump Flow Rate (ml·min⁻¹) | Mobile Phase | UV Wavelength (nm) | Column Temperature (° C.) |
|---|---|---|---|---|
| Salmeterol Xinafoate and Fluticasone Propionate (Dual detection) | 2.0 | Mobile Phase A: 25 mM sodium hydrogen orthophosphate and acetonitrile 80:20 v/v<br>Mobile Phase B: 25 mM sodium hydrogen orthophosphate and acetonitrile 40:60 v/v | 214 | 60 |

The composition of the mobile phase was varied as shown in Table 5 below.

TABLE 5

| Time (mins) | Volume % of Mobile Phase A | Volume % of Mobile Phase B |
|---|---|---|
| 0 | 100 | 0 |
| 32.0 | 0 | 100 |
| 32.1 | 100 | 0 |
| 37.0 | 100 | 0 |

The results of investigating the chemical stability of the salmeterol xinafoate and fluticasone propionate drug formulations in HFA-152a and HFA-227ea in uncoated aluminium cans are shown, respectively, in Tables 6 to 9 below.

TABLE 6

Chemical stability of fluticasone propionate in HFA-134a in uncoated aluminium cans based on percentage assay and total impurities upon storage at T = 0, T = 1M @ 40° C./75% RH and 25° C./60% RH, T = 3M @ 40° C./75% RH and 25° C./60% RH and T = 6M @ 40° C./75% RH and 25° C./60% RH.

| Time | % Assay (LC) | % total impurities |
|---|---|---|
| Initial time T = 0 | 100.8 | <LoQ |
| T = 1M @ 25/60 | 100.1 | <LoQ |
| T = 1M @ 40/75 | 99.9 | <LoQ |
| T = 3M @ 25/60 | 99.8 | <LoQ |
| T = 3M @ 40/75 | 99.8 | <LoQ |
| T = 6M @ 25/60 | 97.2 | 0.32 |
| T = 6M @ 40/75 | 96.5 | 0.48 |

TABLE 7

Chemical stability of fluticasone propionate in HFA-152a in uncoated aluminium cans based on percentage assay and total impurities upon storage at T = 0, T = 1M @ 40° C./75% RH and 25° C./60% RH, T = 3M @ 40° C./75% RH and 25° C./60% RH and T = 6M @ 40° C./75% RH and 25° C./60% RH.

| Time | % Assay (LC) | % total impurities |
|---|---|---|
| Initial time T = 0 | 100.5 | <LoQ |
| T = 1M @ 25/60 | 100.0 | <LoQ |
| T = 1M @ 40/75 | 100.2 | <LoQ |
| T = 3M @ 25/60 | 99.8 | <LoQ |
| T = 3M @ 40/75 | 100.0 | <LoQ |
| T = 6M @ 25/60 | 98.9 | 0.25 |
| T = 6M @ 40/75 | 98.6 | 0.39 |

TABLE 8

Chemical stability of salmeterol xinafoate in HFA-134a in uncoated aluminium cans based on percentage assay and total impurities upon storage at T = 0, T = 1M @ 40° C./75% RH and 25° C./60% RH, T = 3M @ 40° C./75% RH and 25° C./60% RH and T = 6M @ 40° C./75% RH and 25° C./60% RH.

| Time | % Assay (LC) | % total impurities |
|---|---|---|
| Initial time T = 0 | 99.9 | 0.07 |
| T = 1M @ 25/60 | 99.7 | 0.08 |
| T = 1M @ 40/75 | 99.2 | 0.11 |
| T = 3M @ 25/60 | 98.5 | 0.18 |
| T = 3M @ 40/75 | 97.9 | 0.23 |
| T = 6M @ 25/60 | 97.5 | 0.29 |
| T = 6M @ 40/75 | 96.9 | 0.43 |

TABLE 9

Chemical stability of salmeterol xinafoate in HFA-152a in uncoated aluminium cans based on percentage assay and total impurities upon storage at T = 0, T = 1M @ 40° C./75% RH and 25° C./60% RH, T = 3M @ 40° C./75% RH and 25° C./60% RH and T = 6M @ 40° C./75% RH and 25° C./60% RH.

| Time | % Assay (LC) | % total impurities |
|---|---|---|
| Initial time T = 0 | 99.9 | 0.07 |
| T = 1M @ 25/60 | 99.9 | 0.08 |
| T = 1M @ 40/75 | 99.5 | 0.08 |
| T = 3M @ 25/60 | 99.6 | 0.08 |
| T = 3M @ 40/75 | 99.1 | 0.11 |
| T = 6M @ 25/60 | 98.5 | 0.26 |
| T = 6M @ 40/75 | 98.9 | 0.35 |

It can be seen from the data in Tables 6 to 9 above that both salmeterol xinafoate and fluticasone propionate exhibit superior chemical stability when blended with HFA-152a as the aerosolization propellant rather than HFA-134a.

The invention claimed is:

1. A method of improving the stability of a pharmaceutical composition comprising a propellant component and a drug component comprising at least one salmeterol compound selected from salmeterol and the pharmaceutically acceptable salts thereof, said method comprising:
   using a propellant component at least 90 weight % of which is 1,1-difluoroethane (HFA-152a), and
   selecting the components and conditions for the preparation of the pharmaceutical composition to maintain the water content of the pharmaceutical composition below 500 ppm based on the total weight of the pharmaceutical composition.

2. A method of improving the stability of a pharmaceutical composition comprising a propellant component and a drug component comprising at least one salmeterol compound selected from salmeterol and the pharmaceutically acceptable salts thereof, said method comprising:
   using a propellant component at least 90 weight % of which is 1,1-difluoroethane (HFA-152a), wherein the oxygen content of the resulting pharmaceutical composition is below 1000 ppm based on the total weight of the pharmaceutical composition.

3. The method of claim 1, wherein the at least one salmeterol compound is selected from salmeterol and salmeterol xinafoate.

4. The method of claim 1, wherein the drug component additionally comprises at least one long acting muscarinic antagonist (LAMA).

5. The method of claim 4, wherein the at least one long acting muscarinic antagonist is selected from the group consisting of umeclidinium, ipratropium, tiotropium, aclidinium and the pharmaceutically acceptable salts thereof.

6. The method of claim 4, wherein the at least one long acting muscarinic antagonist is a pharmaceutically acceptable salt of glycopyrrolate.

7. The method of claim 1, wherein the drug component additionally comprises at least one corticosteroid.

8. The method of claim 7, wherein the at least one corticosteroid is selected from the group consisting of budesonide, mometasone, beclomethasone, fluticasone and the pharmaceutically acceptable salts and esters thereof.

9. The method of claim 7, wherein the at least one corticosteroid is selected from fluticasone and the pharmaceutically acceptable salts and esters thereof.

10. The method of claim 1, wherein the pharmaceutical composition further comprises a surfactant component comprising at least one surfactant compound.

11. The method of claim 1, wherein the pharmaceutical composition further comprises a polar excipient.

12. The method of claim 11, wherein the polar excipient is ethanol.

13. The method of claim 1, wherein the pharmaceutical composition after storage in uncoated aluminium containers at 40° C. and 75% relative humidity for 6 months will produce less than 0.4% by weight of impurities from the degradation of the at least one salmeterol compound based on the total weight of the at least one salmeterol compound and the impurities.

14. The method of claim 13, wherein at least 98.0% by weight of the at least one salmeterol compound that is contained originally in the pharmaceutical composition immediately following preparation will be present in the composition after storage in uncoated aluminium containers at 40° C. and 75% relative humidity for 6 months.

15. The method of claim 1, wherein the pharmaceutical composition is in the form of a suspension.

16. The method of claim 1, wherein the pharmaceutical composition is stabilised compared to a pharmaceutical composition that uses 1,1,1,2-tetrafluoroethane (HFA-134a) or 1,1,1,2,3,3,3-heptafluoropropane (HFA-227ea) as the propellant but which is otherwise identical.

* * * * *